United States Patent [19]

Horovitz

[11] Patent Number: 5,037,821

[45] Date of Patent: Aug. 6, 1991

[54] METHOD FOR INHIBITING LOSS OF COGNITIVE FUNCTIONS EMPLOYING A CALCIUM CHANNEL BLOCKER ALONE OR IN COMBINATION WITH AN ACE INHIBITOR

[75] Inventor: Zola P. Horovitz, Princeton, N.J.

[73] Assignee: E. R. Squibb & Sons, Inc., Princeton, N.J.

[21] Appl. No.: 328,973

[22] Filed: Mar. 27, 1989

Related U.S. Application Data

[63] Continuation-in-part of Ser. No. 203,173, Jun. 1, 1988, abandoned.

[51] Int. Cl.$^5$ .................... A01N 43/46; A61K 31/55; C07D 223/16; C07D 281/10
[52] U.S. Cl. .................................... 514/211; 514/213; 540/522; 540/523; 546/204
[58] Field of Search .............. 514/211, 213, 411, 413, 514/423; 540/522, 523; 546/204, 208

[56] References Cited

U.S. PATENT DOCUMENTS 4,694,002  9/1987  Floyd et al. ........................ 514/211
4,696,924  7/1986  Marcoux ............................ 514/211
4,748,239  5/1988  Floyd et al. ........................ 540/523

FOREIGN PATENT DOCUMENTS

3610391A1  3/1979  Fed. Rep. of Germany .

OTHER PUBLICATIONS

Qin, W. C. et al., Chung Kuo I Hsueh Ko Hsueh Yuan Hsueh Pao, Oct. 1986, 8 (5) pp. 366-370.
Albizzati, M. G., et al., "Cyclandelate Versus Fulnarizine, a Double-Blind Study in a Selected Group of Patients with Dementia", Drugs 1987, 33 Suppl. 2, 90-96.
Adler, L. et al., "Calcium Channel Antagonists in Tardive Dyskinesia and Psychosis".
Leyd, D. et al., "Diltiazem for Tardive Dyskinesia," The Lancet, Jan. 30, 1988.
Dolin, S. J. et al., "Calcium Channel Antagonists Decrease the Ethanol Withdrawal Syndrome," British Journal of Pharmacology, vol. 87, Mr. Suppl. 40P (1986).
Croog, S. H. et al., "The Effects of Antihypertensive Therapy on the Quality of Life," New England J. of Med. 314:1657-1664 (Jun. 26), 1986.
G. Spinosa et al., "Angiotensin Converting Enzyme Inhibitors: Animal Experiments Suggest a New Pharmacological Treatment for Alcohol Abuse in Humans," Alcoholism: Clinical and Experimental Research, vol. 12, No. 1, Jan./Feb. 1988, pp. 65-70.

Primary Examiner—Merrell C. Cashion, Jr.
Assistant Examiner—Carlos Azpuru
Attorney, Agent, or Firm—Burton Rodney

[57] ABSTRACT

A method is provided for inhibiting loss of cognitive function, including memory, which may or may not be associated with Alzheimer's disease, in a mammalian species by administering a benzazepine-type or a pyrimidine-type calcium channel blocker such as diltiazem, SQ 31,765, SQ 32,324, SQ 33,351, SQ 33,537 or SQ 32,547 alone or in combination with an ACE inhibitor, such as captopril or SQ 29,852, over a prolonged period of treatment.

26 Claims, 6 Drawing Sheets

ACTIONS OF DILTIAZEM AND NIFEDIPINE ON MOUSE HABITUATION

ACTIONS OF DILTIAZEM AND NIFEDIPINE ON MOUSE HABITUATION

METHOD FOR INHIBITING LOSS OF COGNITIVE FUNCTIONS EMPLOYING A CALCIUM CHANNEL BLOCKER ALONE OR IN COMBINATION WITH AN ACE INHIBITOR

This application is a continuation-in-part of U.S. application Ser. No. 203,173, filed June 1, 1988, now abandoned.

FIELD OF THE INVENTION

The present invention relates to a method for inhibiting loss of cognitive functions, including memory, which are associated with different types of dementias in mammalian species by administering a benzazepine-type or a pyrimidine-type calcium channel blocker, such as diltiazem, alone or in combination with an ACE inhibitor, such as captopril, zofenopril, fosinopril or SQ 29,852, over a prolonged period of time.

BACKGROUND OF THE INVENTION

Sudilovsky et al., "Captopril Delays Extinction of Conditional Avoidance Response in the Rat," Poster Presentation, 14th Congress of the Collegium Internationale Neuro-Psychopharmacologicum, Florence, Italy, June, 1984, disclose that after 10 days methyldopa was found to impair conditioned avoidance acquisition in the rat and to accelerate conditioned avoidance extinction, whereas captopril did not affect conditioned avoidance acquisition and significantly delayed conditioned avoidance extinction.

Katz, A. M. et al., "Differential effects of 1,4-dihydropyridine calcium channel blockers," J. Clin. Pharmacol (US), November 1987, 27 (11) 825-34, disclose that selectivity for the cerebrovascular bed makes nimodipine potentially useful in the treatment of dementia.

Albizzati, M. G., et al., "Cyclandelate versus Flunarizine, a double-blind study in a selected group of patients with dementia," Drugs 1987, 33 Suppl. 2, 90-6, disclose that when flunarizine was tested in patients with dementia, improvement was observed in neurological impairment, ischemia scores, Gottfries scale and Hamilton depression scores.

Qin, W. C., et al., in Chung Kuo I Hsueh Ko Hsueh Yuan Hsueh Pao, October 1986, 8(5), 366–70, disclose that nimodipine, nifedipine and vincamine improve amnesia induced by anisodine and sodium nitrite in rats and mice.

U.S. Pat. No. 4,386,095 discloses that certain diaminopyridines improve cognition.

U.S. Pat. No. 4,694,085 discloses that 5,6-dihydropyrrolo(2,1-a)isoquinolines are calcium antagonists and nootropic agents.

UK patent application No. 2,176,788A discloses that certain 2-halonicergoline compounds are calcium antagonists and improve cognitive action of the brain.

DESCRIPTION OF THE INVENTION

In accordance with the present invention, a method is provided for inhibiting loss of cognitive functions such as memory, attention span, concentration and ability to learn or for treating or delaying progression of Alzheimer's disease or other types of dementias, in mammalian species over a prolonged period wherein a therapeutically effective amount of a benzazepinetype or a pyrimidine-type calcium channel blocker alone or in combination with an angiotensin converting enzyme inhibitor (ACE inhibitor) is systemically, such as orally or parenterally, administered over a prolonged period, to inhibit loss of cognitive function during such period.

Where a combination of a calcium channel blocker and ACE inhibitor are to be used, the calcium channel blocker will be employed in a weight ratio to ACE inhibitor of within the range of from about 0.1:1 to about 10:1 and preferably from about 0.4:1 to about 2.5:1.

The calcium channel blocker also referred to as calcium entry blocker or calcium antagonist which is used herein is preferably diltiazem which is disclosed in U. S. Patent No. 3,562,257 and which has the chemical name 3-(acetyloxy)-5-[2-(dimethylamino)ethyl-2,3-dihydro-2-(4-methoxyphenyl)-1,5-benzothiazepin-4(5H)-one and the structure

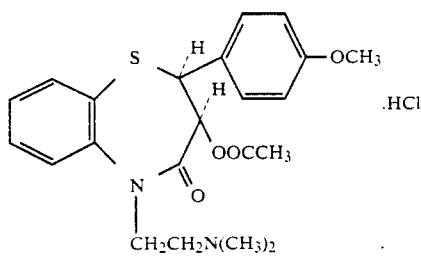

In addition, the calcium channel blocker may be a benzazepine derivative such as disclosed in U.S. Pat. No. 4,748,239 and which has the formula

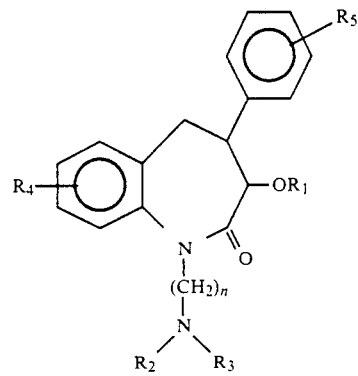

or a pharmaceutically acceptable salt thereof wherein $R_1$ is hydrogen, alkyl, alkanoyl, alkenyl, arylcarbonyl, heteroarylcarbonyl or

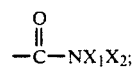

$R_2$ and $R_3$ are each independently hydrogen, alkyl, cycloalkyl or arylalkyl or $R_2$ and $R_3$ together with the nitrogen atom to which they are attached are pyrrolidinyl, piperidinyl, or morpholinyl;

$R_4$ and $R_5$ are each independently hydrogen, halogen, alkyl, alkoxy, aryloxy, arylalkoxy, diarylalkoxy, arylalkyl, cyano, hydroxy, alkanoyloxy,

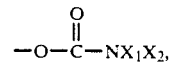

fluoro substituted alkoxy, fluoro substituted alkyl, (cycloalkyl)alkoxy, —NO$_2$, —NX$_3$X$_4$, —S(O)$_m$alkyl, —S-(O)$_m$aryl,

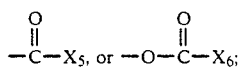

n is 2 or 3;

m is 0, 1 or 2;

X$_1$ and X$_2$ are each independently hydrogen, alkyl, aryl or heteroaryl, or X$_1$ and X$_2$ together with the nitrogen atom to which they are attached are pyrrolidinyl, piperidinyl or morpholinyl;

X$_3$ and X$_4$ are each independently hydrogen, alkyl, alkanoyl, arylcarbonyl, heteroarylcarbonyl,

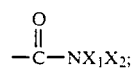

X$_5$ is hydroxy, alkoxy, aryloxy, amino, alkylamino or dialkylamino; and

X$_6$ is alkyl, alkoxy or aryloxy with the proviso that if R$_4$ is a 7-alkyl group, it must have a tertiary carbon atom bonded to the ring;

wherein the term "aryl" refers to phenyl and phenyl substituted with 1, 2 or 3 amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl groups; and the term "heteroaryl" refers to pyridinyl, pyrrolyl, imidazolyl, furyl, thienyl, or thiazolyl.

A preferred such benzazepine derivative had the structure

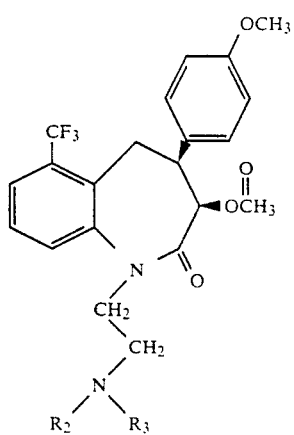

wherein R$_2$ and R$_3$ are each CH$_3$ or one of R$_2$ and R$_3$ is H and the other is CH$_3$, including the hydrochloride salts thereof.

Another class of benzazepine derivatives suitable for use here has the formula

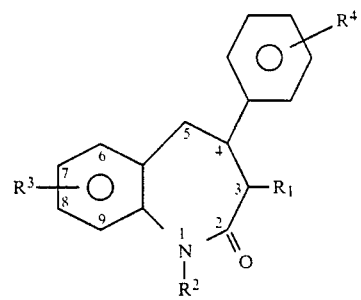

and the pharmaceuticlly acceptable salts thereof, wherein

R$^1$ is $-\overset{Y_1}{\underset{Y_2}{C}}H$ or $-O-Y_3$;

R$^2$ is 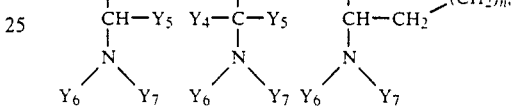

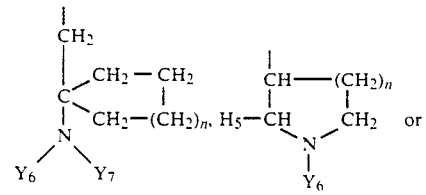

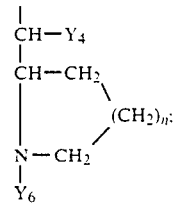

R$^3$ and R$^4$ are each independently hydrogen, halogen, alkyl, alkoxy, aryloxy, arylalkoxy, diarylalkoxy, arylalkyl, cyano, hydroxy, alkanoyloxy,

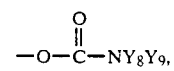

fluoro substituted alkoxy, fluoro substituted alkyl, (cycloalkyl)alkoxy, —NO$_2$, —NY$_{10}$Y$_{11}$, —S(O)$_m$alkyl, —S(O)$_m$aryl,

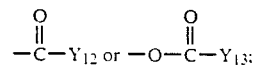

n is 0, 1, 2 or 3;

m is 0, 1 or 2;

Y$_1$ and Y$_2$ are each hydrogen or alkyl, Y$_1$ is hydrogen and Y$_2$ is alkenyl, alkynyl, aryl, heteroaryl, or cycloalkyl, or Y$_1$ and Y$_2$ together with the carbon atom to which they are attached are cycloalkyl;

$Y_3$ is hydrogen, alkyl, alkanoyl, alkenyl, arylcarbonyl, heteroarylcarbonyl, or

$Y_4$ and $Y_5$ are each independently hydrogen, alkyl, aryl or arylalkyl, provided that when both are present they are not both hydrogen, and provided further that when both are attached to the same carbon atom neither of them is hydrogen;

$Y_6$ and $Y_7$ are each independently hydrogen, alkyl, cycloalkyl or arylalkyl or $Y_6$ and $Y_7$ together with the nitrogen atom to which they are attached are azetidinyl, pyrrolidinyl, piperidinyl, or morpholinyl;

$Y_8$ and $Y_9$ are each independently hydrogen, alkyl, aryl or heteroaryl, or $Y_8$ and $Y_9$ together with the nitrogen atom to which they are attached are pyrrolidinyl, piperidinyl or morpholinyl;

$Y_{10}$ and $Y_{11}$ are each independently hydrogen, alkyl, alkanoyl, arylcarbonyl, heteroarylcarbonyl, or

$Y_{12}$ is hydroxy, alkoxy, aryloxy, amino, alkylamino or dialkylamino; and $Y_{13}$ is alkyl, alkoxy or aryloxy.

These compounds are disclosed in U.S. application Ser. No. 208,521, filed June 20, 1988.

Preferred such benzazepines are [3R-[1(S*),3α, 4α]]-3-(acetyloxy)-1,3,4,5-tetrahydro-4-(4-methoxyphenyl)-1-(2-pyrrolidinylmethyl)-6-(trifluoromethyl)-2H-1-benzazepin-2-one or a pharmaceutically acceptable salt thereof, preferably the monohydrochloride and [3(R)-[1(S*),3o,4o]]-1,3,4,5-tetrahydro-3-hydroxy-4-(4-methoxyphenyl)-1-(2-pyrrolidinylmethyl)-6-(trifluoromethyl)-2H-1-benzazepin-2-one, or a pharmaceutically acceptable salt thereof, preferably the monohydrochloride.

The calcium channel blocker may also be a 2-thioxo-4-methyl-6-substituted phenyl-1,5(2H)-pyrimidinedicarboxylic acid ester having the formula

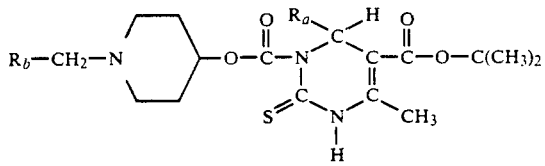

Wherein $R_a$ is 2-(trifluoromethyl)phenyl, 2-chlorophenyl, 2-nitrophenyl, or 3-nitrophenyl and $R_b$ is phenyl, 2-chlorophenyl, or 4-fluorophenyl, which are disclosed in U.S. application Ser. No. 00,618 filed Jan. 5, 1987.

The preferred pyrimidine is the compound (R)-3,6-dihydro-4-methyl-2-thioxo-6-[2-(trifluoromethyl)-phenyl]-1,5(2H)-pyrimidinedicarboxylic acid, 1-[1-[(2-chlorophenyl)methyl]-4-piperidinyl]-5-(1-methylethyl) ester, monohydrochloride, which is prepared using the methodology described in U.S. application Ser. No. 00,618.

Another class of pyrimidine calcium channel blockers suitable for use herein is disclosed in pending application Ser. No. 008,037, filed Feb. 9, 1987, has the formula

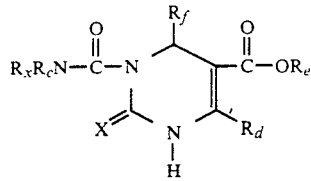

or a pharmaceutically acceptable salt thereof wherein
$X$ is oxygen or sulfur;

$R_x$ is hydrogen, alkyl, cycloalkyl, aryl, or arylalkyl and $R_c$ is hydrogen, alkyl, cycloalkyl, aryl,

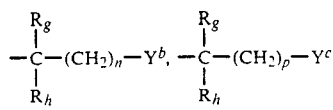

or halo substituted alkyl, or $R_x$ and $R_c$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azeipinyl substituted with alkyl, alkoxy, alkylthio, halo, trifluoromethyl or hydroxy;

$R_d$ is hydrogen, alkyl, alkenyl, alkynyl, cycloalkyl, aryl

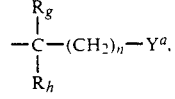

or halo substituted alkyl;

$R_e$ is hydrogen, alkyl, cycloalkyl, aryl,

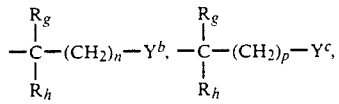

or halo substituted alkyl;

$R_f$ 2,1,3-benzoxadiazol-4-yl, phenyl, or phenyl substituted with one, two or three alkyl, halo, nitro, cyano, amino, dialkylamino, trifluoromethyl, isothiocyanato or isocyanato groups;

$R_g$ and $R_h$ are each independently hydrogen, alkyl, $-(CH_2)_{q1}$-aryl or $-(CH_2)_{q1}$-cycloalkyl;

$Y^a$ is cycloalkyl, aryl, hydroxyl, alkoxy, aryl-$(CH_2)_m$—O—, mercapto, alkylthio, aryl-$(CH_2)_m$—S—, amino, substituted amino, carbamoyl,

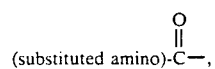

carboxyl, alkoxycarbonyl,

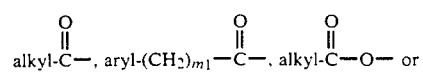

-continued

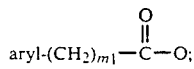

$Y^b$ is cycloalkyl, aryl, carbamoyl,

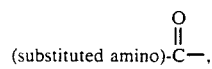

carboxyl, alkoxycarbonyl,

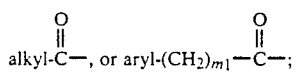

$Y^c$ is hydroxyl, alkoxy, aryl-$(CH_2)_{m1}$—O—, mercapto, alkylthio, aryl-$(CH_2)_{m1}$—S—,

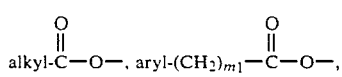

amino, or substituted amino;

$q_1$ is 0, 1, 2 or 3;

$m_1$ is 0 or an integer of 1 to 6;

$n_1$ is 0 or an integer of 1 to 5; and $p_1$ is an integer of 1 to 5; wherein the term "cycloalkyl" refers to a cycloalkyl group having 3,4,5,6 or 7 carbon atoms;

the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;

the term "substituted amino" refers to a group of the formula —$NZ_1Z_2$ wherein $Z_1$ is hydrogen, alkyl, or aryl-$(CH_2)_{m1}$— and $Z_2$ is alkyl or aryl-$(CH_2)_{m1}$—.

Preferred is the compound having the name (R)-1-(aminocarbonyl)-4-(3-chlorophenyl)-1,2,3,4-tetrahydro-6-methyl-2-oxo-5-pyrimidinecarboxylic acid, 1-methylethyl ester.

The method of the invention is useful in treating or delaying progression of primary degenerative dementias arising in the senium and presenium such as Alzheimer's disease, Pick's disease and Binswanger's disease, and vascular dementias such as arteriolsclerotic dementias including multiple infarct dementia and Binswanger's disease.

The angiotensin converting enzyme inhibitor which may be employed herein includes substituted proline derivatives, such as any of those disclosed in U.S. Pat. No. 4,105,776 to Ondetti et al mentioned above, with captopril, that is, 1-[(2S)-3-mercapto-2-methylpropionyl]-L-proline, being preferred, carboxyalkyl dipeptide derivatives, such as any of those disclosed in U.S. Pat. No. 4,374,829, with N-(1-ethoxycarbonyl-3-phenylpropyl)-L-alanyl-L-proline, that is, enalapril, being preferred.

Other examples of angiotensin converting enzyme inhibitors suitable for use herein include any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline (SQ 29,852) being preferred, phosphinylalkanoyl prolines disclosed in U.S. Pat. No. 4,168,267 with fosinopril being preferred, mercaptoacyl derivatives of substituted prolines disclosed in U.S. Pat. No. 4,316,906 with zofenopril being preferred, any of the phosphinylalkanoyl substituted prolines disclosed in U.S. Pat. No. 4,337,201, and the phosphonamidates disclosed in U.S. Pat. No. 4,432,971.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]]3R(*)]-2-[2-[[1-(ethoxycarbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

The disclosure of the above-mentioned U.S. patents are incorporated herein by reference.

In carrying out the method of the present invention, calcium channel blocker alone or in combination with the angiotensin converting enzyme inhibitor may be administered to mammalian species, such as monkeys, dogs, cats, rats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the calcium channel blocker in an amount within the range of from about 0.01 mg/kg to about 100 mg/kg and preferably from about 0.1 mg/kg to about 25 mg/kg alone or in combination with the ACE inhibitor in an amount within the range of from about 0.01 mg/kg to about 100 mg/kg and preferably from about 0.1 mg/kg to about 25 mg/kg with the calcium channel blocker and ACE inhibitor being employed together in the same oral dosage form or in separate oral dosage forms taken at the same time.

A preferred oral dosage form, such as tablets or capsules, will contain the calcium channel blocker in an amount of from about 0.1 to about 500 mg, preferably from about 125 to about 200 mg, and more preferably from about 25 to about 150 mg, alone or with the ACE inhibitor in an amount of from about 1 to about 350 mg, preferably from about 2 to about 200 mg, and more preferably from about 30 to about 150 mg.

For parenteral administration, the calcium channel blocker will be employed in an amount within the range of from about 0.005 mg/kg to about 10 mg/kg and preferably from about 0.01 mg/kg to about 1 mg/kg, alone or with the ACE inhibitor in an amount within the range of from about 0.005 mg/kg to about 20 mg/kg and preferbly from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 10 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of calcium channel blocker and ACE inhibitor are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil.

Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for onset of loss of cognitive function remains or the symptoms continue. Sustained release forms of such formulations which may provide such amounts biweekly, weekly, monthly and the like may also be employed. A dosing period of at least one to two weeks are required to achieve minimal benefit.

Figure 1:
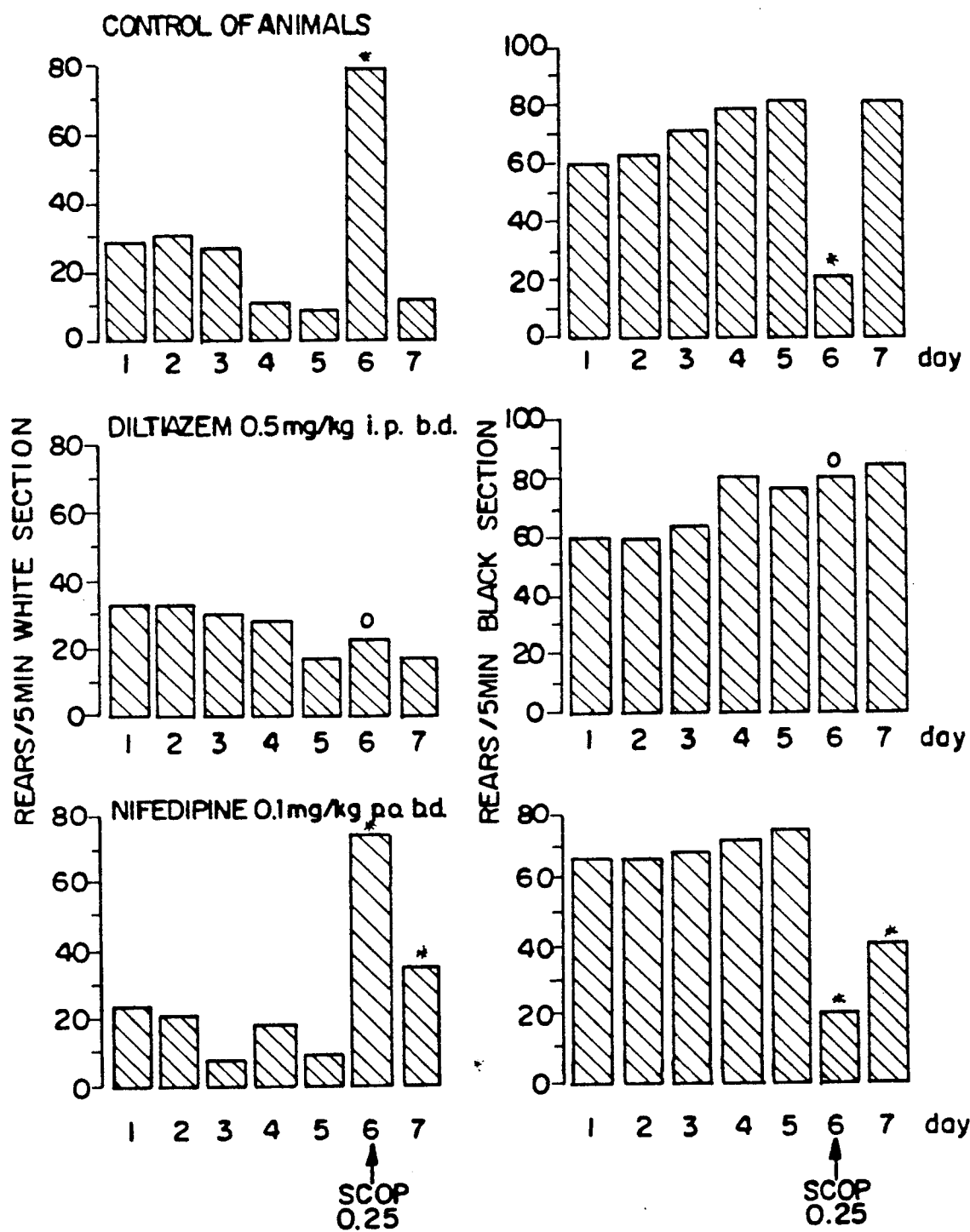
FIGS. 1 to 3 are graphs showing actions of diltiazem and nifedipine on mouse habituation.

The following Examples represent preferred embodiments of the present invention.

EXAMPLE 1

A diltiazem formulation suitable for oral administration in inhibiting loss of cognitive functions is set out below.

1000 tablets each containing 100 mg of diltiazem were produced from the following ingredients.

| | |
|---|---|
| Diltiazem | 100 g |
| Corn starch | 50 g |
| Gelatin | 7.5 g |
| Avicel (microcrystalline cellulose) | 25 g |
| Magnesium stearate | 2.5 g |

The diltiazem and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for inhibiting loss of cognitive functions.

EXAMPLE 2

1000 tablets each containing 50 mg of SQ 32,324 are produced from the following ingredients:

| | |
|---|---|
| (d-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, monohydrochloride salt (SQ 32,324) | 50 g |
| Lactose | 100 g |
| Avicel | 150 g |
| Corn starch | 50 g |
| Magnesium stearate | 5 g |

SQ 32,324 lactose and Avicel are admixed, then blended with the corn starch. Magnesium stearate is added. The dry mixture is compressed in a tablet press to form 1000 505 mg tablets each containing 50 mg of active ingredient. The tablets are coated with a solution of Methocel E 15 (methyl cellulose) including as a color a lake containing yellow #6. The resulting tablets are useful in inhibiting loss of cognitive functions.

EXAMPLE 3

Two piece #1 gelatin capsules each containing 40 mg of diltiazem are filled with a mixture of the following ingredients:

| Diltiazem | 40 mg |
|---|---|
| Magnesium stearate | 7 mg |
| USP lactose | 193 mg. |

The resulting capsules are useful in inhibiting loss of cognitive functions.

EXAMPLE 4

An injectable solution for use in inhibiting loss of cognitive functions is produced as follows:

| (d-cis)-3-(acetyloxy)-1-[2-dimethyl-amino)ethyl]-1,3,4,5-tetrahydro-4-(4-methoxyphenyl)-6-(trifluoromethyl)-2H-1-benzazepin-2-one, monohydrochloride (SQ 31,765) | 500 mg |
|---|---|
| Methyl paraben | 5 mg |
| Propyl paraben | 1 mg |
| Sodium chloride | 25 g |
| Water for injection qs. | 5 l. |

SQ 31,765, preservatives and sodium chloride, are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 0.1 mg of active ingredient per ml of solution for injection.

EXAMPLE 5

A captopril-diltiazem formulation suitable for oral administration in inhibiting loss of cognitive function is set out below.

1000 tablets each containing 100 mg of 1-[(2S)-3-mercapto-2-methylpropionyl]-L-proline and 100 mg of diltiazem are produced from the following ingredients:

| 1-(2S)-3-mercapto-2-methylpropionyl]-L-proline (captopril) | 100 g |
|---|---|
| Diltiazem | 100 g |
| Corn starch | 50 g |
| Gelatin | 7.5 g |
| Avicel (microcrystalline cellulose) | 25 g |
| Magnesium stearate | 2.5 g |

The captopril, diltiazem and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 200 mg of active ingredients which is used for inhibiting loss of cognitive function.

EXAMPLE 6

By substituting 100 g of 1-(3-mercapto-2-D-methylpropanoyl)-L-proline for the captopril in Example 5, 1000 tablets each containing 100 mg of the 1-(3-mercapto-2-D-methylpropanoyl)-L-proline and 100 mg diltiazem are produced which is useful in inhibiting loss of cognitive function.

EXAMPLE 7

1000 tablets each containing 200 mg of SQ 29,852 and 100 mg SQ 32,324 are produced from the following ingredients:

| SQ 29,852 | 200 g |
|---|---|
| SQ 32,324 | 100 g |
| Lactose | 100 g |
| Avicel | 150 g |
| Corn starch | 50 g |
| Magnesium stearate | 5 g |

The SQ 29,852, SQ 32,324, lactose and Avicel are admixed, then blended with the corn starch. Magnesium stearate is added. The dry mixture is compressed in a tablet press to form 1000 505 mg tablets each containing 200 mg of SQ 29,852 and 100 mg of SQ 32,324. The tablets are coated with a solution of Methocel E 15 (methyl cellulose) including as a color a lake containing yellow #6. The resulting tablets are useful in inhibiting loss of cognitive function.

EXAMPLE 8

An injectable solution for use in treating or preventing loss of cognitive function is produced as follows:

| SQ 29,852 | 500 mg |
|---|---|
| Diltiazem | 500 mg |
| Methyl paraben | 5 g |
| Propyl paraben | 1 g |
| Sodium chloride | 25 g |
| Water for injection qs. | 5 L. |

The SQ 29,852, diltiazem, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 0.1 mg of each active ingredient per ml of solution for injection.

EXAMPLE 9

Tablets for use in inhibiting loss of cognitive function are prepared as described in Example 5 except that N-(1-ethoxycarbonyl-3-phenylpropyl)-L-alanyl-L-proline (enalapril) is used in place of captopril and SQ 32,324 is used in place of diltiazem.

EXAMPLE 10

Tablets for use in inhibiting loss of cognitive function are prepared following the procedure of Example 5 except that zofenopril is employed in place of captopril.

EXAMPLE 11

Tablets for use in inhibiting loss of cognitive function are prepared following the procedure of Example 5 except that fosinopril is employed in place of captopril.

EXAMPLE 12

Tablets for use in inhibiting loss of cognitive function are prepared following the procedure of Example 5 except that SQ 29,852 is employed in place of captopril.

EXAMPLE 13

1000 tablets each containing 100 mg of the benzazepine derivative SQ 33,351 are produced from the following ingredients:

| | |
|---|---|
| [3R-[1(S*),3α,4α]]-3-(acetyloxy)-1,3,4,5-tetrahydro-4-(4-methoxyphenyl)-1-(2-pyrrolidinylmethyl)-6-(trifluoromethyl)-2H-1-benzazepin-2-one monohydrochloride (SQ 33,351) | 100 g |
| Lactose | 100 g |
| Avicel | 150 g |
| Corn starch | 50 g |
| Magnesium stearate | 5 g |

SQ 33,351, lactose and Avicel are admixed, then blended with the corn starch. Magnesium stearate is added. The dry mixture is compressed in a tablet press to form 1000 505 mg tablets each containing 100 mg of active ingredient. The tablets are coated with a solution of Methocel E 15 (methyl cellulose) including as a color a lake containing yellow #6. The resulting tablets are useful in inhibiting loss of cognitive functions.

EXAMPLE 14

Two piece #1 gelatin capsules each containing 50 mg of SQ 33,537 are filled with a mixture of the following ingredients:

| | |
|---|---|
| [3(R)-[1(S*),3α,4α]]-1,3,4,5-tetrahydro-3-hydroxy-4-(4-methoxyphenyl)-1-(2-pyrrolidinylmethyl)-6-(trifluoromethyl)-2H-1-benzazepin-2-one, monohydrochloride (SQ 33,537) | 50 mg |
| Magnesium stearate | 7 mg |
| USP lactose | 193 mg |

The resulting capsules are useful in inhibiting loss of cognitive functions.

EXAMPLE 15

1000 tablets each containing the following ingredients:

| | |
|---|---|
| (R)-3,6-Dihydro-4-methyl-2-thioxo-6-[2-(trifluoromethyl)phenyl]-1,5(2H)pyrimidinedicarboxylic acid, 1-[1-[(4-fluorophenyl)methyl]-4-piperidinyl] 5-(1-methylethyl) ester, monohydrochloride (SQ 32,547) | 40 mg |
| Corn starch | 50 mg |
| Gelatin | 7.5 mg |
| Avicel(microcrystalline cellulose) | 25 mg |
| Magnesium stearate | 2.5 mg | were prepared from sufficient bulk quantities by mixing the (R)-3,6-dihydro-4-methyl-2-thioxo-6-[2-(trifluoromethyl)phenyl]-1,5(2H)-pyrimidinedicarboxylic acid, 1-[1-[(4-fluorophenyl)methyl]-4-piperidinyl] 5-(1-methylethyl) ester, monohydrochloride and cornstarch with an aqueous solution of the gelatin. The mixture was dried and ground to a fine powder. The Avicel and then the magnesium stearate were admixed with granulation. This mixture was then compressed in a tablet press to form 1000 tablets each containing 40 mg of active ingredient.

A similar procedure can be employed to form tablets containing 60 mg of active ingredient.

The so-formed tablets may be used for inhibiting loss of cognitive function.

EXAMPLE 16

A tablet formulation for use in inhibiting loss of cognitive function is prepared using the procedure as described in Example 15 except SQ 32,926 is used as the calcium channel blocker.

SQ 32,926 was prepared as follows.

(R)-1-(Aminocarbonyl)-4-(3-chlorophenyl)-1,2,3,4-tetrahydro-6-methyl-2-oxo-5-pyrimidinecarboxylic acid, 1-methylethyl ester (SQ 32,926)

A. 1,4-Dihydro-4-(3-chlorophenyl)-2-methoxy-6-methyl-5-pyrimidinecarboxylic acid, 1-methylethyl ester, oxalate salt A mixture of 3-chlorobenzaldehyde (49.20 g, 350 mmol), isopropyl acetoacetate (50.46 g, 350 mmol), magnesium sulfate (52.5 g), acetic acid (3.5 mL), and piperidine (7.0 mL) in dichloromethane (350 mL) in a 2 l three-necked flask under argon was mechanically stirred at room temperature for 20 hours. The reaction was filtered, the filter cake was rinsed heavily with dichloromethane (filtrate volume 1.2 l), and the filtrate was washed with 1N sodium hydroxide (75 mL), 1N hydrochloric acid (100 mL), 10% sodium bisulfite (200 mL), saturated sodium chloride (100 mL), dried (magnesium sulfate), and evaporated to give crude Knovenagel product as a yellow foam (96.0 g).

The crude Knovenagel product (~350 mmol) was taken up in dimethylformamide (175 mL) in a 2 l three-necked flask under argon, treated with sodium bicarbonate (88.21 g, 1.05 mol), and then treated portionwise with O-methylisourea hydrogen sulfate (78.33 g, 455 mmol) over the next 1 hour. The reaction was then heated at 75° C (oil bath) overnight under argon. The reaction was cooled, diluted with chloroform (875 mL), filtered (filter cake rinsed thoroughly with chloroform), and evaporated. The thick oily residue was distilled in vacuo at 50° C. (oil bath) to remove most of the dimethylformamide. The resulting residue was taken up in ethyl acetate (1.5 l) and washed with water (5 x 250 mL), saturated sodium chloride (2 x 250 mL), dried (magnesium sulfate), and evaporated to give a light yellow oil (127.5 g). This oil was dissolved in dichloromethane (175 mL), diluted with isopropanol, and evaporated until only isopropanol remained (final volume about 175 mL). This solution was then treated with a solution of oxalic acid (31.51 g, 350 mmol) in isopropanol (175 mL) and the resulting solid was filtered to give the title compound (69.76 g), melting point 131°-133° C.

B. 1,2,3,4-Tetrahydro-4-(3-chlorophenyl)-6-methyl-3-[[(4-nitrophenyl)oxy]carbonyl]-5-pyrimidinecarboxylic acid, 1-methylethyl ester 1,4-Dihydro-4-(3-chlorophenyl)-2-methoxy-6-methyl-5-pyrimidinecarboxylic acid, 1-methylethyl ester, oxalate salt (68.75 g, 166.5 mmol) was partitioned between chloroform (1 l) and 10% sodium carbonate solution (240 mL), shaken thoroughly, and the layers separated. The aqueous phase was reextracted with chloroform (2 x 300 mL). The combined organic phases were dried (magnesium sulfate) and evaporated to give the free base as a yellow oil.

This free base was transferred (chloroform, 330 mL) to a 2l 3-necked flask fitted with a mechanical stirrer and flushed with argon. The solution was treated with sodium bicarbonate (84.0 g, 1.00 mol) and then treated portionwise over the next 1.5 hours with 4-nitrophenyl-chloroformate (40.31 g, 200 mmol). After stirring at room temperature overnight, the reaction was filtered through a pad of Celite and evaporated to give a yellow foam. The foamy residue was taken up in a tetrahydrofuran (666 mL) and treated with 3N hydrochloric acid (67 mL, 200 mmol). After stirring for 0.5 hours, the reaction was partially evaporated. The residue was -partitioned between ethyl acetate (1.6 l) and water 100 mL). The organic phase was washed with 10% sodium carbonate (3 x 100 mL portions), saturated sodium chloride (2 x 100 mL), dried (magnesium sulfate), and evaporated. The residue was taken up in dichloromethane, diluted with methanol (about 700 mL), and partially evaporated to give the title compound (53.14 g), melting point 165–167° C. A second crop (8.91 g) precipitated from the partially concentrated mother liquor. The two crops were again taken up in dichloromethane, diluted with methanol, and partially evaporated to give the title compound as colorless crystals (56.35 g), melting point 167°–168° C.

C. (R)-4-(3-Chlorophenyl)-1,2,3,4-tetrahydro-6-methyl-2-oxo-1-[[(1-phenylethyl)amino]carbonyl]-5-pyrimidinecarboxylic acid, 1-methylethyl ester A mixture of 1,2,3,4-tetrahydro-4-(3-chlorophenyl)-6-methyl-3-[[(4-nitrophenyl)oxy]carbonyl]5-pyrimidinecarboxylic acid, 1-methylethyl ester (56.00 g, 118 mmol) in acetonitrile (472 mL) under argon was treated with S-(−)-α-methylbenzyl amine (16.76 mL, 130 mmol). After stirring for 0.75 hours, the reaction was evaporated. The residue was taken up in ethyl acetate and washed with 1N sodium hydroxide (4 x 200 mL), saturated sodium chloride (2 x 100 mL portions), 10% citric acid (200 mL), saturated sodium chloride (100 mL), dried (magnesium sulfate), and evaporated. The residue was crystallized from isopropyl ether (about 900 mL) to give colorless crystals (21.39 g), melting point 198°–200° C. Recrystallization gave the title compound as colorless crystals (20.13 g), melting point 200°–201° C. $\alpha_D = -273°$ (c=1,chloroform).

D. (R)-1-(Aminocarbonyl)-4-(3-chlorophenyl)1,2,3,4-tetrahydro-6-methyl-2-oxo-5-pyrimidinecarboxylic acid, 1-methylethyl ester A solution (dissolved upon heating) of (R)-4-(3-chlorophenyl)-1,2,3,4-tetrahydro-6-methyl-2-oxo-1-[[(1-phenylethyl)amino]carbonyl]-5-pyrimidinecarboxylic acid, 1-methylethyl ester (18.85 g, 41.34 mmol) in trifluoroacetic acid (40 mL) under argon was heated at 75° C. (oil bath) for 2.0 hours. The reaction was cooled and evaporated. The residue was coevaporated with toluene (twice). The residue was taken up in ethyl acetate (750 mL) and washed with saturated sodium bicarbonate, saturated sodium chloride, dried (magnesium sulfate), and evaporated. The residue was crystallized from isopropyl ether to give colorless crystals (11.15 g), melting point 165°–166° C. A second crop (2.40 g), melting point 163°–165° C., was combined with the first crop (total 13.54 g) and recrystallized from isopropyl ether to give the title compound as colorless crystals (11.45 g), melting point 167°–168° C.

$[\alpha]_D = -157°$ (c=1.0, methanol).

Analysis calc'd for $C_{16}H_{18}N_3O_4Cl$:
C, 54.62; H, 5.16; N, 11.95; Cl, 10.08.
Found: C, 54.49; H, 5.18; N, 11.57; Cl, 10.07.

EXAMPLE 17

The following experiments are carried out to demonstrate the effectiveness of benzazepine-type calcium channel blockers alone and ACE inhibitors alone in inhibiting loss of cognitive functions.

Adult male Sprauge-Dawley rats (Charles River, Wilmington, Mass.), age 25 weeks and weighing 350–400 g, are separately housed in stainless steel cages with continuous access to food and water, a 12-hour light-dark cycle, and constant room temperature of 22° to 24° C. All testing took place approximately 6 hours into the dark component of the light-dark cycle and is conducted in a dimly lighted soundproof room using a standard shuttle box device (Lehigh Valley Electronics #146-04), a plexiglass chamber (50 x 20 x 20 cm) divided by a center barrier 7 cm in height. The conditioned stimulus consists of a 10-second tone provided by a Sonlert mounted in the midpoint of the ceiling of the chamber. Floor current of 0.8 mA is delivered by a constant current shocker-scrambler (Lehigh Valley Electronics #133-33).

The day before the initiation of training each animal is allowed to explore the experimental chamber for 10 minutes without any tone or shock. Training is conducted for 15 days following the day of experimental chamber exploration. Each animal receives 20 trials per day on a 30-second variable interval schedule. No drug treatment is administered during the training period. Shock could be avoided by shuttling from one side of the center barrier to the other during the 10-second tone period. If an animal does not cross the center barrier during this period, the tone remains on and the floor shock is delivered until the animal escapes to the other half of the chamber. Animals which consistently remain on the center barrier are removed from the study. Automatic counters record the number of avoidance responses, escapes, and intertrial crossings, while a running time meter records the total shock duration for each animal.

Animals not meeting the admittance criterion of correct avoidance rsponding on at least 85% of the trials for 4 out of the last 5 days of training are removed from the study. A total of 99 rats reaching the admittance criterion are tested for extinction of conditioned avoidance response (CAE) during 14 days. They are randomly assigned to captopril (ACE inhibitor) (10 mg/kg and 30 mg/kg), zofenopril (ACE inhibitor) (10 mg/kg and 30 mg/kg), fosinopril (ACE inhibitor) (10 mg/kg and 30 mg/kg), methyldopa (no ACE inhibiting acitivty) (10 mg/kg and 30 mg/kg), epicaptopril (a derivative of captopril which does not have ACE inhibiting activity) (10 mg/kg and 30 mg/kg), diltiazem (10 mg/kg and 30 mg/kg) and saline control with each test group at each dosage comprising 9 rats. All solutions are prepared fresh and administered i.p. (1 mg/ml volume) on the 2 days prior to testing and then 1 hour before it. Testing consists of 20 trials per day identical to those previously described, except that no shock is administered if an animal fails to shuttle during the 10-second tone period. The tone is simply discontinued and the testing proceeded.

Two-way analysis of variance of the CAE data yields an overall significant difference in the rate of shuttle extinction between treatment groups.

From the above test, it may be seen that diltiazem and ACE inhibitors, namely, fosinopril, zofenopril and captopril possess protective effects on memory of previously learned tasks while compounds such as epicaptopril and methyldopa which do not have ACE inhibiting activity do not have protective effects against loss of memory of previously learned tasks.

It will also be appreciated that all of the above compounds and formulations and including combinations of calcium channel blocker and ACE inhibitor possess protective effects on memory and may be employed in treating or delaying progression of Alzheimer's disease.

In addition, the calcium channel blocker may be a benzazepine derivative such as disclosed in U.S. Pat. No. 4,748,239, such as SQ 32,324 and SQ 31,765.

EXAMPLE 18

The following experiments were carried out to demonstrate the effectiveness of diltiazem to improve cognition and cognitive impairment.

ABILITY TO IMPROVE BASIC PERFORMANCE AND TO ANTAGONIZE A SCOPOLAMINE IMPAIRMENT IN A MOUSE HABITUATION TEST Methods The studies used a black:white test box procedure as described below. Male albino (BKW) mice were used, initially weighing 25-30 g. In their home cage, mice were housed in groups of 10 and given free access to food and water. The mice were kept on a 12 hour light and 12 hour dark cycle with lights off at 8:00 a.m. and on at 8:00 p.m.

The test box consisted of an open-topped box (45 x 27 x 27 cm), 40% of the area painted black and illuminated with a dim red light (1 x 60 W), the other painted white and brightly illuminated with white light (1 x 60 W) located 17 cm above the box. Access between the two areas was enabled by means of a 7.5 x 7.5 cm opening located at floor level in the center of the partition (which also served to prevent diffusion of light between the two compartments of the test box). The floor area was lined into 9 cm squares.

The habituation test was carried out daily by placing mice in the center of the white section of the test box (mice taken from dark home environment in a dark container, to the experimental room maintained in low red lighting, and would normally be averse to the bright white conditions). Testing was carried out between 8:30 and 12:30 p.m. The test period was 5 minutes per day. Behavior was assessed via remote video recording, and the following measures taken:

1. Latency to move from the white to the black section (sec).
2. Numbers of exploratory rears in the white and black sections during the 5 minute test.
3. Numbers of line crossings (exploratory locomotion) in the white and black sections during the 5 minute test.
4. Time spent in the black section of the box during the 5 minute test.
5. Numbers of transitions between the black and white sections of the test box during the 5 minute test (since this parameter was not changed in any situation in the present studies, data for transitions is not given or commented on further).

Generally, as animals habituated to the test system, they would move into the black section of the box where behavioral exploration was exhibited as exploratory rears and line crossings.

Scopolamine was used at a dose of 0.25 mg/kg i.p. to disrupt habituation patterns. This could be achieved by a single acute challenge with scopolamine which disrupted the learning patterns on the day of treatment, with subsequent recovery, or by continued daily treatment with scopolamine 1 hour before test. The dose of scopolamine was carefully selected as one which did not cause autonomic disturbance (0.25 mg/kg i.p. methyl scopolamine failed to influence behavior). Under the influence of 0.25 mg/kg i.p. scopolamine mice would go to the door in the partition, investigate the opening and pass the head or body through, but without association of the dark environment with escape from the brightly-lit averse environment.

Results.

The normal learning curve for mice in the habituation test was 5-6 days as evidenced by reduced rearings and line crossings in the white compartment, increased in the black, reduced latency to move to the black and increased % of time spent in the black. Acutely administered scopolamine causes impairment in control animals. Example data is given here for rears: mice had 'learned' to avoid the white averse environment and by day 6 were carrying out most of their behavior in the black—this was prevented by scopolamine which caused an impairment characterized by increased activity in the white, decreased in the black. This impairment caused by scopolamine can be prevented by arecoline. The selection of dose and route for arecoline are critical to avoid unwanted autonomic disturbance The arecoline is given continuously by intraperitoneal infusion from Alzet osmotic minipumps at a dose of 50 mg/kg/day. It is interesting that while the continuous treatment with this dose of arecoline inhibited the scopolamine impairment of habituation, the time course of the basic 'learning' or habituation was unaffected by the presence of arecoline. This contrasts with findings for the diltiazem.

Using the same procedure as described above, control mice and mice treated with diltiazem were subject to the habituation procedure and challenged with scopolamine on days 6 and 10. Firstly, it was seen that the basal learning procedure was speeded by treatment with diltiazem. Secondly, the treatments with diltiazem were shown to completely antagonize the impairments caused by scopolamine.

Assessments of the potential of hydergine to improve cognitive function in the mouse habituation test utilized the same test protocol as described so far for arecoline and diltiazem Hydergine was obtained as a proprietary product and the human dose titrated to mouse for single daily challenge, orally, 60 minutes before test. Treatment with hydergine was clearly shown to enhance 'learning' in the mouse habituation test. Rearing in the white section rapidly diminished as this behavior correspondingly increased in the black, and crossings in the white decreased significantly below control values by day 2 of testing, again with corresponding increases in the black and increased % of time in the black was significant on day 2 as were the reductions in latencies to move from the white to the black section on days 2, 3 and 4 of testing.

The treatment with hydergine was not associated with any anxiolytic potential and the dose regime was maintained constant at 0.1 mg/kg p.o. daily. After 4 days some motor impairment and sedation developed in a small proportion of animals; this particularly influenced the latency to move from the white environment and data for such animals had to be excluded from analyses.

A very important observation was that while hydergine (like diltiazem but in contrast to arecoline) could enhance basal learning, it was not able to antagonize the influence of scopolamine to impair performance whether measured as changed rearing, changed line crossings or changed % time in black, and latency to move out of the white, aversive environment. This failure to antagonize, indeed, to any way influence the impairment caused by scopolamine contrasts with the marked antagonistic effects of arecoline and diltiazem.

In a further series of experiments mice were allowed to habituate for 10 days and then were challenged daily with scopolamine, 0.25mg/kg. The habituation was impaired throughout the time of scopolamine challenge. If, after impairment with scopolamine was established, mice were given arecoline (50 mg/kg/day by intraperitoneal infusion from Alzet osmotic minipumps), or diltiazem daily with the scopolamine treatment, then the scopolamine impairment was completely prevented.

CONCLUSIONS Assessment of Ability to Improve Cognition and Cognitive Impairment

A mouse habituation test was used in which mice were repeatedly placed in the white compartment of a white:black test box. On repeated
exposure to the test situation, mice 'learn' to avoid the averse white, brightly-lit environment and move rapidly into the black where they spend a larger proportion of time and show most exploratory rearings and line crossings.

The habituation (learning) time is 5-6 days. This basic 'learning' time was not influenced by arecoline (50 mg/kg/day given by continuous intraperitoneal infusion: dose and route selected to avoid unwanted autonomic effects). However, this dose of arecoline successfully antagonised an impairment in habituation caused by acute challenge with scopolamine (0.25 mg/kg i.p., dose again carefully selected to avoid excessive peripheral autonomic disturbance, and particularly to avoid influence on vision which can influence performance in the test: lack of effect on vision was established by visual observation and by measurement of pupil function). Methyl scopolamine at a dose of 0.25 mg/kg i.p. failed to influence mouse habituation. The effect of scopolamine was marked: animals which had learned to avoid the white environment failed to enter the black, excepting for short periods of time, even though they easily found the door, and thus the rapid exit into the black and avoidance of the white environment was prevented by scopolamine treatment.

In contrast to arecoline, the speed of habituation was enhanced by treatment with low doses of diltiazem. Diltiazem was found to antagonize the impairment in habituation performance caused by acute challenge with scopolamine.

Hydergine (0.1 mg/kg p.o. once daily) was shown to speed the habituation process in a similar manner to diltiazem (both in contrast to the failure of arecoline), but hydergine treatment failed to influence the impairment in habituation caused by acute challenge with scopolamine (which contrasts with the actions of both diltiazem and the cholinomimetic agent).

Further studies allowed habituation to progress for 10 days before continuous impairment by scopolamine given daily for up to 14 days. This persistent impairment caused by scopolamine could be antagonized by arecoline (50 mg/kg/day by intraperitoneal infusion) and by diltiazem.

EXAMPLE 19

Actions of Diltiazem and Nifedipine on Mouse Habituation (FIGS. 1 to 3) Methods

The methodologies described for habituation in Example 18 were employed throughout a 7 day habituation period; diltiazem or nifedipine were given continuously at doses of 0.5 mg/kg i.p. b.d. and 0.1 mg/kg p.o. b.d., respectively. Animals were given an acute challenge with scopolamine, 0.25 mg/kg i.p., on the 6th day of habituation.

Results

Control mice showed the usual habituation patterns. Thus, by day 4-5 they had learned to move rapidly from the aversive white environment to the preferred black environment. This is seen as progressively reduced rears in the white section with corresponding increases in the black (FIG. 1), reduced line crossings in the white with increases in the black (FIG. 2), increased % of time spent in the black (FIG. 3) and reduced latency for the initial move from the white to the black environment (FIG. 3).

Figure 2:
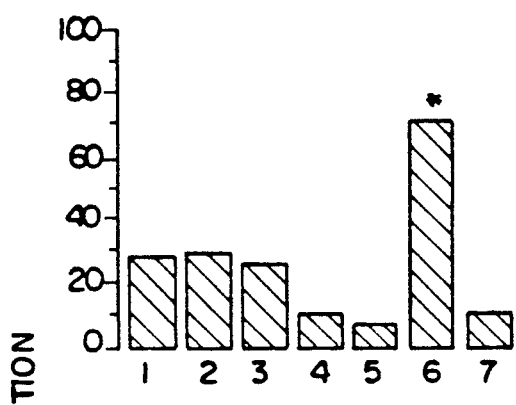
Figure 2:
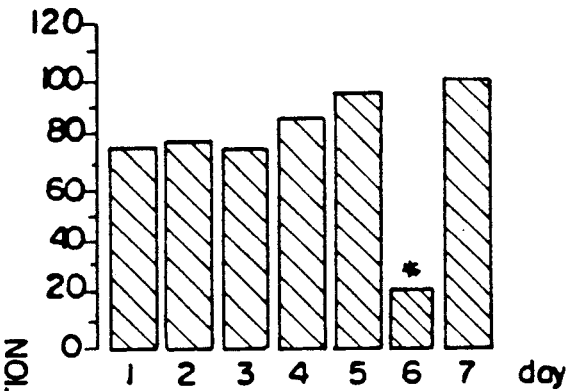
Figure 2:
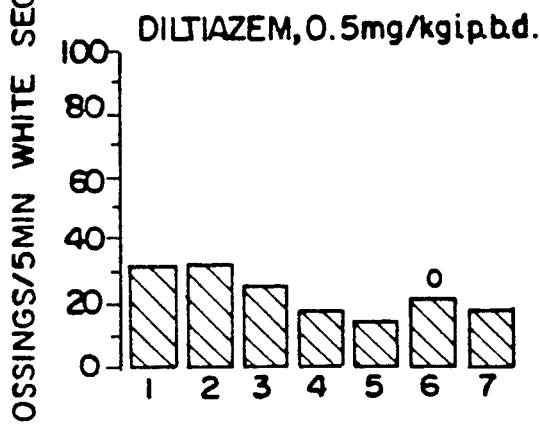
Figure 2:
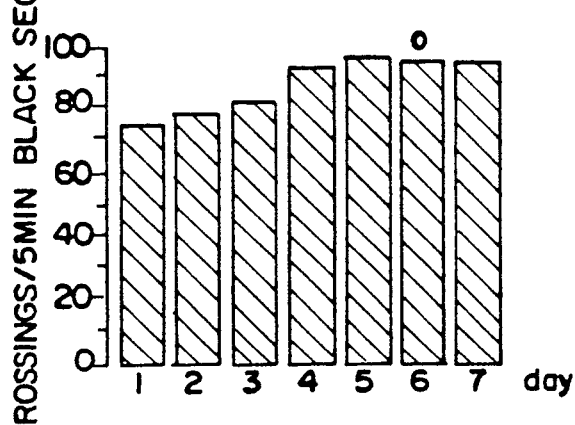
Figure 2:
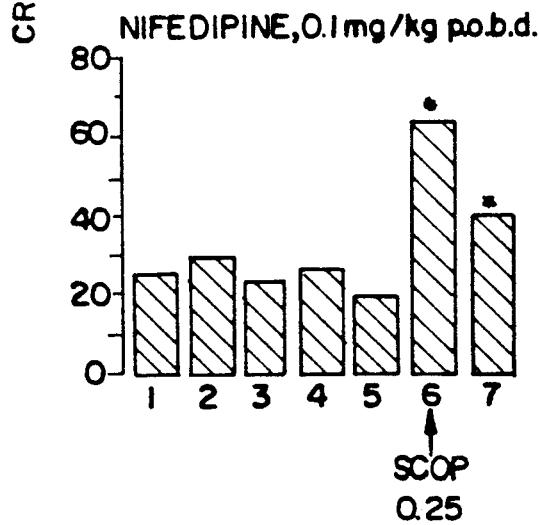
Figure 2:
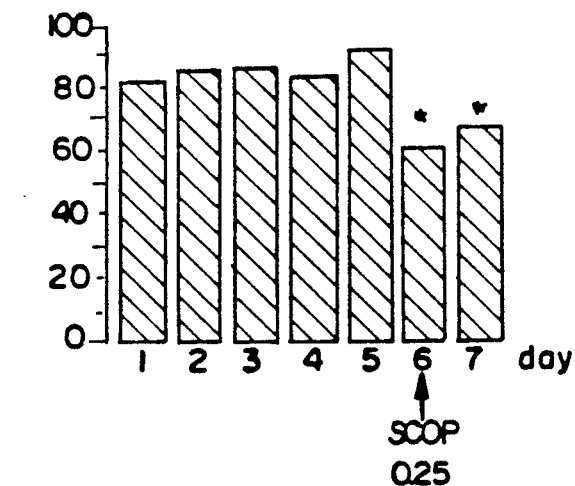
Figure 3:
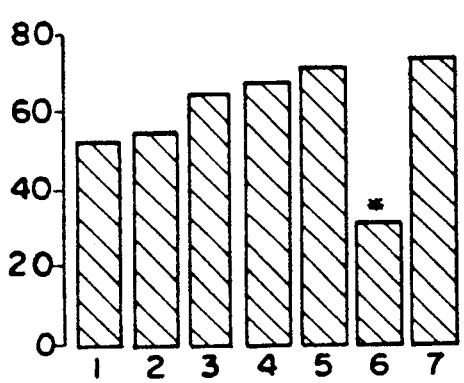
Figure 3:
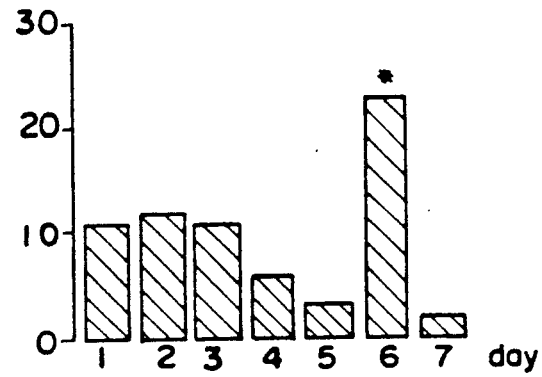
Figure 3:
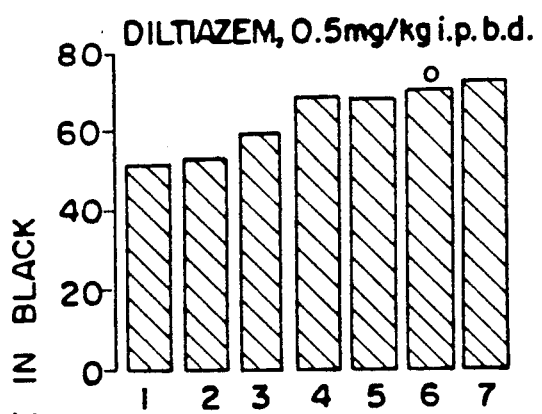
Figure 3:
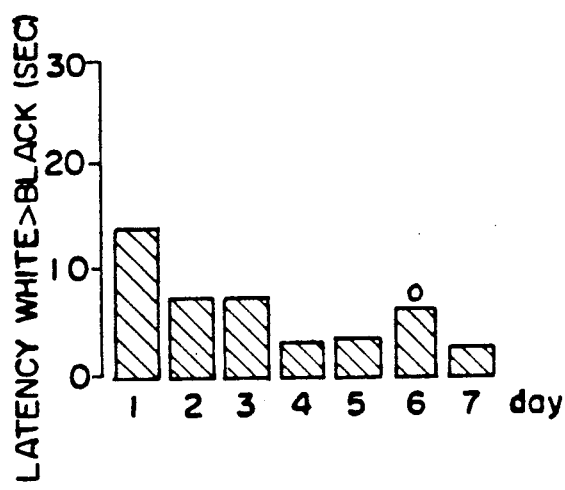
Figure 3:
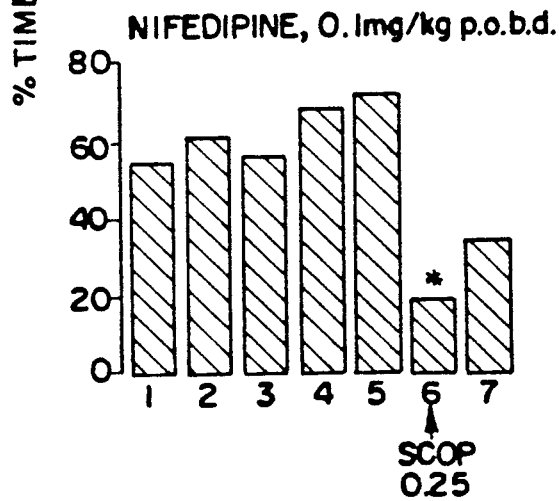
Figure 3:
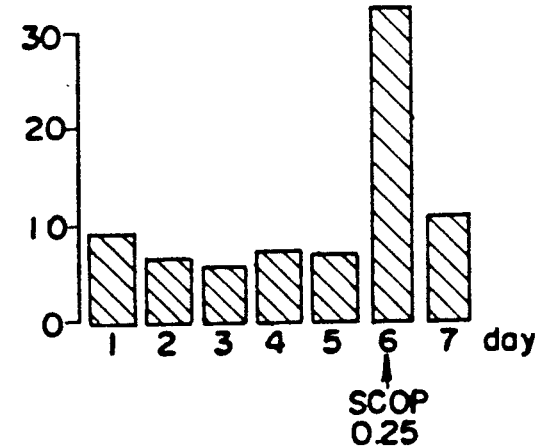

The treatment with diltiazem or nifedipine failed to influence these basal habituation patterns (FIGS. 1, 2 and 3) but the impairment in habituation patterns caused by scopolamine in control animals was completely prevented in the animals which had received continuous treatment with diltiazem (seen for rears on FIG. 1, line crossings on FIG. 2, % time in black and latency to move from the white to the black on FIG. 3). In contrast to diltiazem, nifedipine treatments failed to protect against the scopolamine impairments (FIGS. 1, 2 and 3). Indeed, these tended to be more persistent in the nifedipinetreated animals (FIGS. 1, 2 and 3).

Conclusions

Whilst the calcium channel blockers, at the doses used, failed to modulate basal learning, diltiazem treatment was shown to prevent an impairment in mouse cognitive performance caused by scopolamine. This protection against an anticholinergic impairment was not seen for nifedipine. Nevertheless, the present data provides an indication that the calcium channel blockers may have effects on the central nervous system which could be therapeutically useful.

EXAMPLE 20

Actions of SQ 33,351 and 33,537 on Mouse Habituation Methods

The methodologies described for habituation in Example 18 were employed throughout a 6 day habituation; SQ 33,351 or SQ 33,537 were given continuously at doses of 0.1 mg/kg i.p. b.d. and 0.1 mg/kg p.o. b.d., respectively. Animals were given an acute challenge with scopolamine, 0.25 mg/kg i.p., on the 6th day of habituation.

Results

Figure 4:
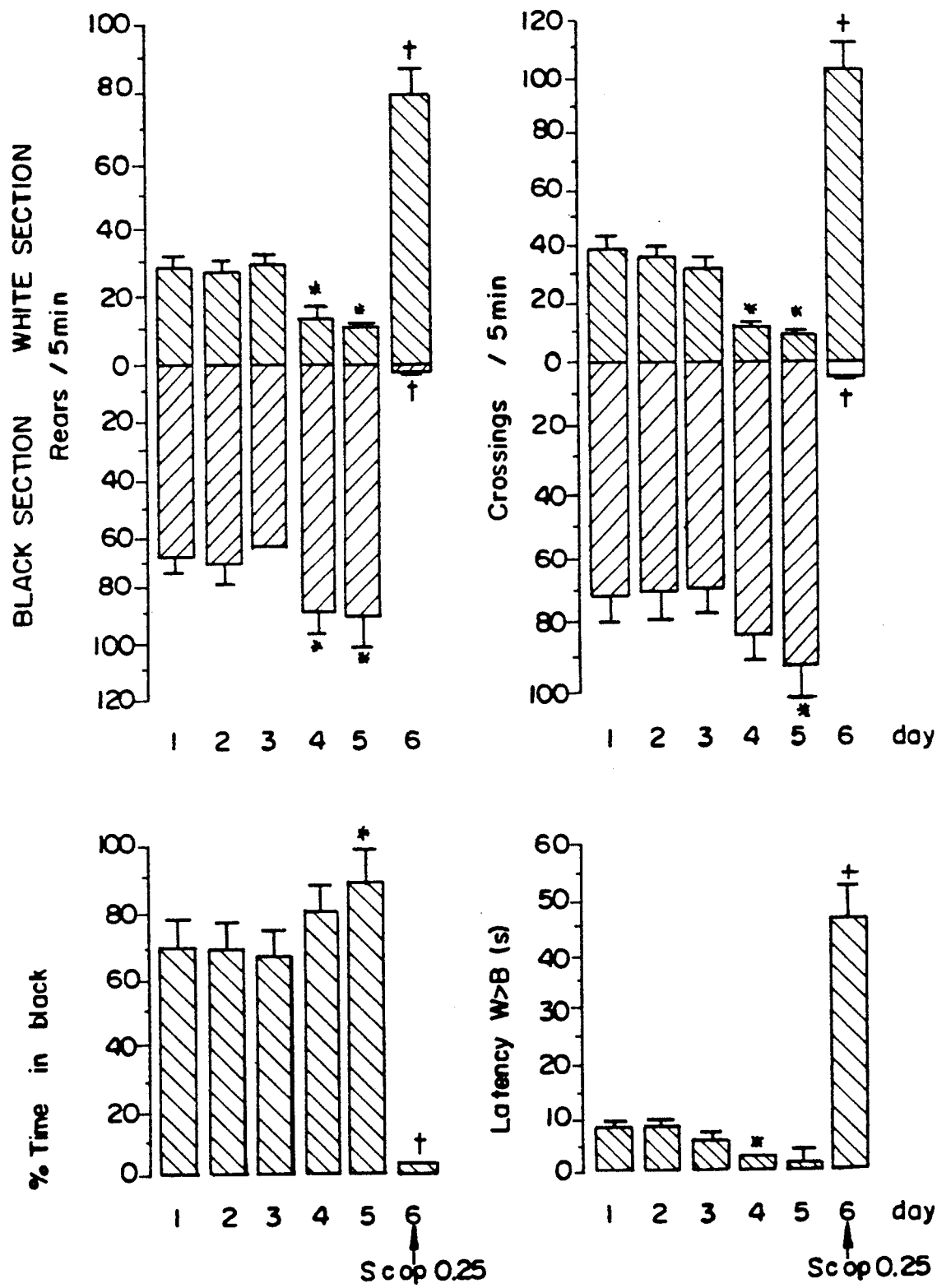
FIGS. 4, 5 and 6 are graphs showing actions of scopolamine (FIG. 4), SQ 33,351 (FIG. 5), and SQ 33,537 (FIG. 6) on mouse habituation.

Control mice showed the usual habituation patterns. Thus, by day 4-5 they had learned to move rapidly from the aversive white environment to the preferred black environment. This is seen as progressively reduced rears in the white section with corresponding increases in the black (FIG. 4), reduced line crossings in the white with increases in the black (FIG. 4), increased % of time spent in the black (FIG. 4) and reduced latency for the initial move from the white to the black environment (FIG. 4).

Figure 5:
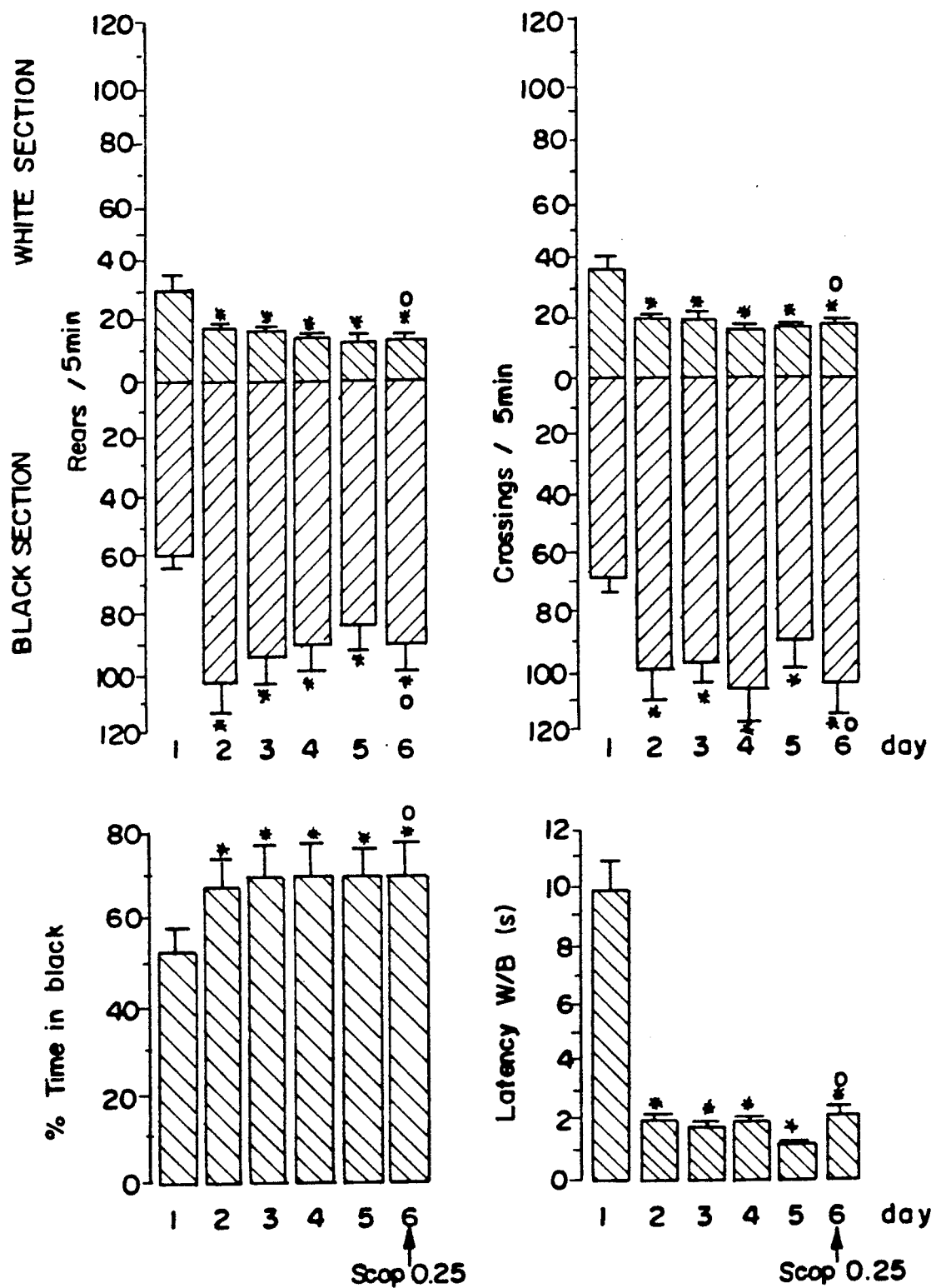
Figure 6:
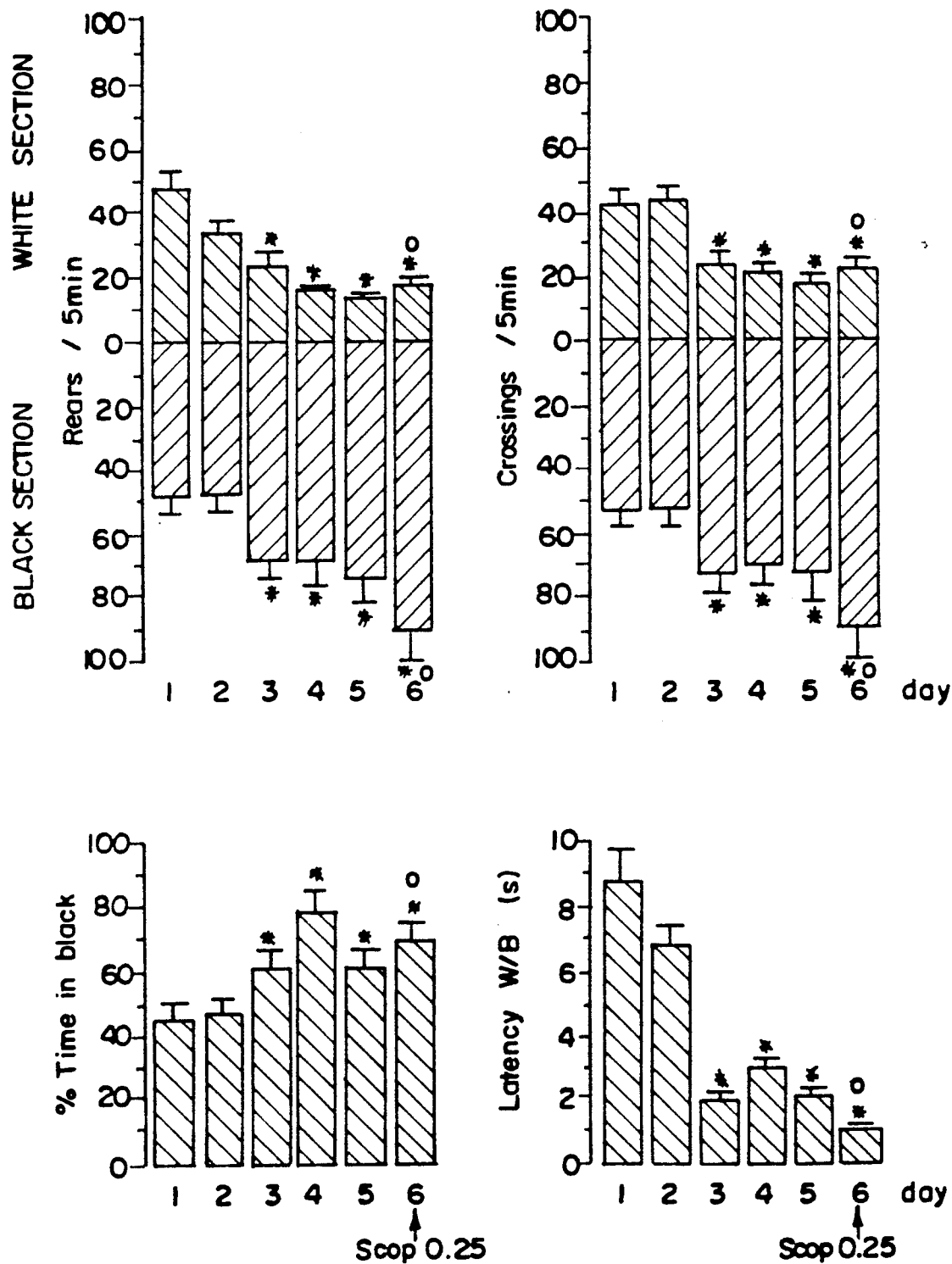

The treatment with SQ 33,351 or SQ 33,537 completely prevented the impairment in habituation patterns caused by scopolamine in control animals seen for rears, line crossings, % time in black and latency to move from the white to the black on FIG. 5 for SQ 33,351 and FIG. 6 for SQ 33,537.

What is claimed is:

1. A method for inhibiting loss of cognitive function in a mammalian specie over a prolonged period of time, which comprises orally or parenterally administering to a mammalian specie in need of such treatment an effective amount of a benzazepine-type or a pyrimidine-type calcium channel blocker alone or in combination with an angiotensin converting enzyme inhibitor over a prolonged period of treatment to inhibit loss of cognitive function during such period of treatment.

2. The method as defined in claim 1 where the calcium channel blocker is of the benzazepine type.

3. The method as defined in claim 2 wherein the calcium channel blocker is diltiazem.

4. The method as defined in claim 2 wherein the calcium channel blocker has the formula

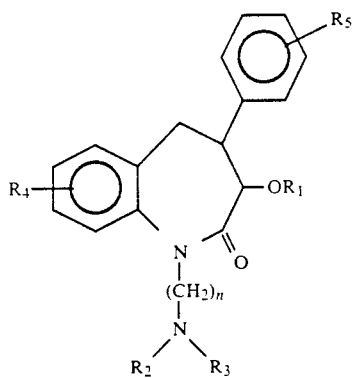

or a pharmaceutically acceptable salt thereof wherein $R_1$ is hydrogen, alkyl, alkanoyl, alkenyl, arylcarbonyl, heteroarylcarbonyl or

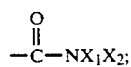

$R_2$ and $R_3$ are each independently hydrogen, alkyl, cycloalkyl or arylalkyl or $R_2$ and $R_3$ together with the nitrogen atom to which they are attached are pyrrolidinyl, piperidinyl, or morpholinyl;

$R_4$ and $R_5$ are each independently hydrogen, halogen, alkyl, alkoxy, aryloxy, arylalkoxy, diarylalkoxy, arylalkyl, cyano, hydroxy, alkanoyloxy,

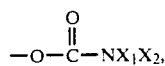

fluoro substituted alkoxy, fluoro substituted alkyl, (cycloalkyl)alkoxy, $-NO_2$, $-NX_3X_4$, $-S(O)_m$alkyl, $-S(O)_m$aryl,

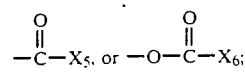

n is 2 or 3;
m is 0, 1 or 2;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl, or

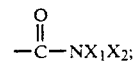

$X_5$ is hydroxy, alkoxy, aryloxy, amino, alkylamino or dialkylamino; and $X_6$ is alkyl, alkoxy or aryloxy; with the proviso that if $R_4$ is a 7-alkyl group, it must have a tertiary carbon atom bonded to the ring;

wherein the term "aryl" refers to phenyl and phenyl substituted with 1, 2 or 3 amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl groups;

the term "heteroaryl" refers to pyridinyl, pyrrolyl, imidazolyl, furyl, thienyl, or thiazolyl.

5. The method as defined in claim 4 wherein the calcium channel blocker is (d-cis)-3-(acetyloxy)-1-[2-dimethylamino)ethyl]-1,3,4,5-tetrahydro-4-(4-methoxyphenyl)-6-(trifluoromethyl)-2H-1-benzazepin-2-one, monohydrochloride (SQ 31,765) or (d-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, monohydrochloride salt (SQ 32,324).

6. The method as defined in claim 2 wherein the calcium channel blocker has the formula

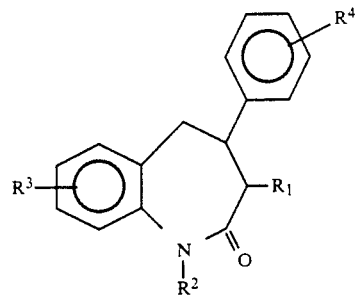

and a pharmaceuticlly acceptable salt thereof, wherein $R^1$ is $-\overset{Y_1}{\underset{Y_2}{CH}}-$ or $-O-Y_3$;

$R^2$ is $\overset{CH-Y_4,}{\underset{CH-Y_5}{\underset{N}{|}}}$ $\overset{CH_2}{\underset{Y_4-C-Y_5}{\underset{N}{|}}}$, $\overset{CH-CH_2}{\underset{CH-CH_2}{\underset{N}{|}}}(CH_2)_n$, $Y_6 \quad Y_7 \quad Y_6 \quad Y_7 \quad Y_6 \quad Y_7$ -continued

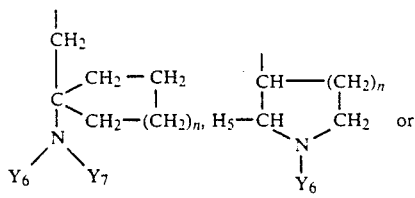

R³ and R⁴ are each independently hydrogen halogen, alkyl, alkoxy, aryloxy, arylalkoxy, diarylalkoxy, arylalkyl, cyano, hydroxy, alkanoyloxy,

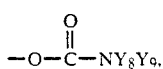

fluoro substituted alkoxy, fluoro substituted alkyl, (cycloalkyl)alkoxy, $-NO_2$, $-NY_{10}Y_{11}$, $-S(O)_m$alkyl, $-S(O)_m$aryl,

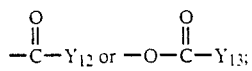

n is 0, 1, 2 or 3;
m is 0, 1 or 2;
$Y_1$ and $Y_2$ are each hydrogen or alkyl, $Y_1$ is hydrogen and $Y_2$ is alkenyl, alkynyl, aryl, heteroaryl, or cycloalkyl, or $Y_1$ and $Y_2$ together with the carbon atom to which they are attached are cycloalkyl;
$Y_3$ is hydrogen, alkyl, alkanoyl, alkenyl, arylcarbonyl, heteroarylcarbonyl, or

$Y_4$ and $Y_5$ are each independently hydrogen, alkyl, aryl or arylalkyl, provided that when both are present they are not both hydrogen, and provided further that when both are attached to the same carbon atom neither of them is hydrogen;
$Y_6$ and Y are each independently hydrogen alkyl, cycloalkyl or arylalkyl or $Y_6$ and $Y_7$ together with the nitrogen atom to which they are attached are azetidinyl, pyrrolidinyl, piperidinyl, or morpholinyl;
$Y_8$ and $Y_9$ are each independently hydrogen, alkyl, aryl or heteroaryl, or $Y_8$ and $Y_9$ together with the nitrogen atom to which they are attached are pyrrolidinyl, piperidinyl or morpholinyl;
$Y_{10}$ and $Y_{11}$ are each independently hydrogen, alkyl, alkanoyl, arylcarbonyl, heteroarylcarbonyl, or

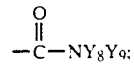

$Y_{12}$ is hydroxy, alkoxy, aryloxy, amino, alkylamino or dialkylamino; and
$Y_{13}$ is alkyl, alkoxy or aryloxy.

7. The method as defined in claim 6 wherein the benzazepine is [3R-[1(S*),3α,4α]]-3-(acetyloxy)-1,3,4,5-tetrahydro-4-(4-methoxyphenyl)-1-(2-pyrrolidinylmethyl)-6-(trifluoromethyl)-2H-1-benzazepin-2-one or a pharmaceutically acceptable salt thereof, or [3(R)-[1(S*),3α,4α]]-1,3,4,5-tetrahydro-3-hydroxy-4-(4-methoxyphenyl)-1-(2-pyrrolidinylmethyl)-6-(trifluoromethyl)-2H-1-benzazepin-2-one, or a pharmaceutically acceptable salt thereof.

8. The method as defined in claim 1 wherein the calcium channel blocker is of the pyrimidine type.

9. The method as defined in claim 8 wherein the pyrimidine-type calcium channel blocker has the formula

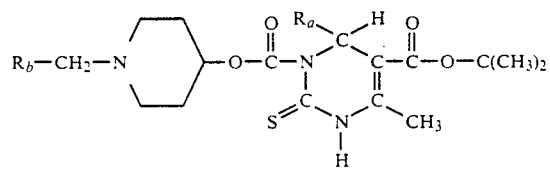

including a pharmaceutically acceptable salt thereof wherein:
$R_a$ is 2-(trifluoromethyl)phenyl, 2-chlorophenyl, 2-nitrophenyl, or 3-nitrophenyl;
and $R_b$ is phenyl, 2-chlorophenyl, or 4-fluorophenyl.

10. The method as defined in claim 9 wherein the pyrimidine is (R)-3,6-dihydro-4-methyl-2-thioxo-6-[2-(trifluoromethyl)phenyl]-1,5(2H)-pyrimidinedicarboxylic acid, 1-[1-[(4-fluorophenyl)methyl]-4-piperidinyl]-5-(1-methylethyl) ester, monohydrochloride.

11. The method ad defined in claim 1 wherein the pyrimidine-type calcium channel blocker has the formula

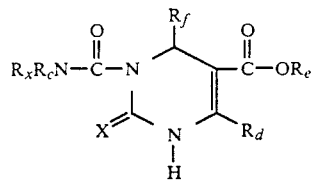

or a pharmaceutically acceptable salt thereof wherein
X is oxygen or sulfur;
$R_x$ is hydrogen, alkyl, cycloalkyl, aryl, or arylalkyl and $R_c$ is hydrogen, alkyl, cycloalkyl, aryl,

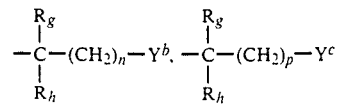

or halo substituted alkyl,
or $R_x$ and $R_c$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azeipinyl substituted with alkyl, alkoxy, alkylthio, halo, trifluoromethyl or hydroxy;

$R_d$ is hydrogen, alkyl, alkenyl, alkynyl, cycloalkyl, aryl

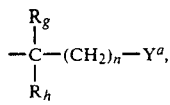

or halo substituted alkyl;

$R_e$ is hydrogen, alkyl, cycloalkyl, aryl,

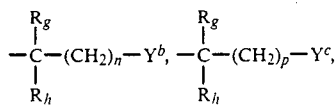

or halo substituted alkyl;

$R_f$ is 2,1,3-benzoxadiazol-4-yl, phenyl, or phenyl substituted with one, two or three alkyl, halo, nitro, cyano, amino, dialkylamino, trifluoromethyl, isothiocyanato or isocyanato groups;

$R_g$ and $R_h$ are each independently hydrogen, alkyl, —$(CH_2)_{q1}$—aryl or —$(CH_2)_{q1}$—cycloalkyl;

$Y^a$ is a cycloalkyl, aryl, hydroxyl, alkoxy, aryl-$(CH_2)_m$—O—, mercapto, alkylthio, aryl-$(CH_2)_m$—S—, amino, substituted amino, carbamoyl,

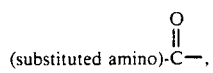

carboxyl, alkoxycarbonyl,

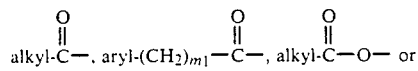 or

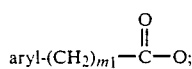

$Y^b$ is cycloalkyl, aryl, carbamoyl,

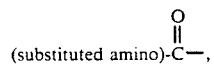

carboxyl, alkoxycarbonyl,

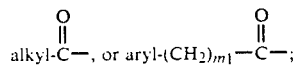

$Y^c$ is hydroxyl, alkoxy, aryl-$(CH_2)_{m1}$—O—, mercapto, alkylthio, aryl-$(CH_2)_{m1}$—S—,

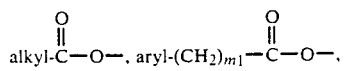

amino, or substituted amino;
$q_1$ is 0, 1, 2 or 3;
$m_1$ is 0 or an integer of 1 to 6;
$n_1$ is 0 or an integer of 1 to 5; and $p_1$ is an integer of 1 to 5; wherein
the term "cycloalkyl" refers to a cycloalkyl group having 3,4,5,6 or 7 carbon atoms;
the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;
the term "substituted amino" refers to a group of the formula —$NZ_1Z_2$ wherein $A_1$ is hydrogen, alkyl, or aryl—$(CH_2)_{m1}$—and $Z_2$ is alkyl or aryl—$(CH_2)_{m1}$—.

12. The method as defined in claim 11 wherein the calcium channel blocker has the name (R)-1-(aminocarbonyl)-4-(3-chlorophenyl)-1,2,3, 4-tetrahydro-6-methyl-2-oxo-5-pyrimidinecarboxylic acid, 1-methylethyl ester.

13. The method as defined in claim 1 wherein the angiotensin converting enzyme inhibitor is a phosphonate substituted amino or imino acid of salt thereof,, a substituted proline derivative, a mercaptoacyl derivative of a substituted proline, a carboxyalkyl dipeptide derivative, a phosphinylalkanoyl proline derivative or a phosphonamidate derivative.

14. The method as defined in claim 1 wherein a calcium channel blocker alone or in combination with said angiotensin converting enzyme inhibitor is administered orally.

15. The method as defined in claim 1 wherein a calcium channel blocker alone or in combination with said angiotensin converting enzyme inhibitor is admixed with a pharmaceutically acceptable carrier therefor and the resulting composition is administered orally.

16. The method as defined in claim 1 wherein said angiotensin converting enzyme inhibitor is a substituted proline derivative.

17. The method as defined in claim 1 wherein said angiotensin converting enzyme inhibitor is a carboxyalkyl dipeptide derivative.

18. The method as defined in claim 1 wherein said angiotensin converting enzyme inhibitor is a phosphinylalkanoyl proline derivative.

19. The method as defined in claim 1 wherein said angiotensin converting enzyme inhibitor is a phosphonamidate derivative.

20. The method as defined in claim 1 wherein said angiotensin converting enzyme inhibitor is a phosphonate substituted amino or imino acid or salt thereof.

21. The method as defined in claim 1 wherein said angiotensin converting enzyme inhibitor is captopril, enalapril, 1-[N-[hydroxy-(4-phenylbutyl)phosphinyl]-2-alanyl]-L-proline or its disodium salt, SQ 29,852, zofenopril, fosinopril or (S)-1-[6-amino-2-[[hydroxy(4-phenylbutyl)phosphinyl]oxy]-1-oxohexyl]-L-proline.

22. The method as defined in claim 1 wherein a calcium channel blocker alone or in combination with said angiotensin converting enzyme inhibitor is administered in the form of tablets or capsules.

23. The method as defined in claim 1 wherein said calcium channel blocker is diltiazem, (d-cis)-3-(acetyloxy)-1-[2-dimethylamino)ethyl]-1,3,4,5-tetrahydro-4-(4-methoxyphenyl)-6-(trifluoromethyl)-2H-1-benzazepin-2-one, monohydrochloride (SQ 31,765), (d-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, monohydrochloride salt (SQ 32,324), [3R-[1(S*),3α, 4α]]-3-(acetyloxy)-1,3,4,5-tetrahydro-4-(4-methoxyphenyl)-1-(2-pyrrolidinylmethyl)-6-(trifluoromethyl)-2H-1-benzazepin-2-one, monohydrochloride salt (SQ 33,351), [3(R)-[1(S*),3α, 4Oα]]-1,3,4,5-tetrahydro-3-hydroxy-4-(4-methoxyphenyl)-1-(2-pyrrolidinylmethyl)-6-(trifluoromethyl)-2H-1-benzazepin-2-one, monohydrochloride salt (SQ 33,537), (R)-3,6-dihydro-4-methyl- 2-thioxo-6-[2-(trifluoromethyl)phenyl]-1,5(2H)-pyrimidinedicarboxylic acid, 1-[1-[(2-chlorophenyl)methyl]-4-piperidinyl]5-(1-methylethyl) ester, monohydrochloride (SQ 32,547) or (R)-1-(aminocarbonyl)-4-(3-chlorophenyl)-1,2,3,4-tetrahydro-6-methyl-2-oxo-5-pyrimidinecarboxylic aicd, 1-methylethyl ester (SQ 32,926) and is administered systemically in an amount of from about 0.1 to about 500 mg/1 to 4 times a day and when present said angiotensin converting enzyme inhibitor is captopril and is administered systemically in an amount of from about 0.1 to about 500 mg/1 or 4 times a day.

24. A method for treating or delaying progression of Alzheimer's disease in a mammalian specie, which comprises administering to a mammalian specie in need of such treatment an effective amount of a benzazepine-type calcium channel blocker alone or in combination with an angiotensin converting enzyme inhibitor.

25. The method as defined in claim 24 wherein said calcium channel blocker alone or in combination with an angiotensin converting enzyme inhibitor is administered over a prolonged period of treatment to inhibit loss of cognitive function during such period of treatment.

26. The method as defined in claim 24 wherein the calcium channel blocker is diltiazem, (d-cis)-3-(acetyloxy)-1-[2-dimethylamino)ethyl]-1,3,4,5-tetrahydro-4-(4-methoxyphenyl)-6-(trifluoromethyl)-2H-1-benzazepin-2-one, monohydrochloride (SQ 31,765), (d-cis)-3-(acetyloxy)-1,3,4,5-tetrahydro-4-(4-methoxyphenyl)-1-[2 -(methylamino)ethyl]-6-(trifluoromethyl)-2H-1-benzazepin-2-one, monohydrochloride salt (SQ 32,324), [3R-[1(S*),3α, 4α]]-3-(acetyloxy)-1,3,4,5-tetrahydro-4-(4-methoxyphenyl)-1-(2-pyrrolidinylmethyl)-6-(trifluoromethyl)-2H-1-benzazepin-2-one monohydrochloride salt (SQ 33,351), [3(R)-[1(S*),3α, 4α]]-1,3,4,5-tetrahydro-3-hydroxy-4-(4-methoxyphenyl)-1-(2-pyrrolidinylmethyl)-6-(trifluoromethyl)-2H-1-benzazepin-2-one, monohydrochloride salt (SQ 33,537), or (R)-3,6-dihydro-4-methyl-2-thioxo-6-[2-(trifluoromethyl)phenyl]-1,5(2H)-pyrimidinedicarboxylic acid, 1-[1-[(2chlorophenyl)methyl]-4-piperidinyl]5-(1-methylethyl) ester, monohydrochloride (SQ 32,547) or (R)-1-(aminocarbonyl)-4-(3-chlorophenyl)-1,2,3,4-tetrahydro-6-methyl-2-oxo-5-pyrimidinecarboxylic aicd, 1-methylethyl ester (SQ 32,926) and when present the angiotensin converting enzyme inhibitor is captopril, SQ 29,852, zofenopril, fosinopril, enalapril or (S)-1-[6-amino-2-[[hydroxy(4-phenylbutyl)phosphinyl]oxy]-1-oxohexyl-L-proline.

* * * * *

UNITED STATES PATENT AND TRADEMARK OFFICE
CERTIFICATE OF CORRECTION

PATENT NO. : 5,037,821

DATED : August 6, 1991

INVENTOR(S) : Zola P. Horovitz

It is certified that error appears in the above-identified patent and that said Letters Patent is hereby corrected as shown below:

Column 11, line 1, please insert a comma (,) between "SQ 32,324" and "lactose".

In the Claims:

Column 23, in the second structure, please change "$H_5$" to --$Y_5$--;

Column 23, line 21, please insert a comma (,) between "hydrogen" and "halogen";

Column 23, line 57, please change "Y" to --$Y_7$--;

Column 28, line 19, please change "1-[1-" to --1-[2- --.

Signed and Sealed this

Twelfth Day of January, 1993

Attest:

DOUGLAS B. COMER

Attesting Officer   Acting Commissioner of Patents and Trademarks